United States Patent
White et al.

(10) Patent No.: US 11,510,709 B2
(45) Date of Patent: Nov. 29, 2022

(54) METHODS AND APPARATUS FOR TREATING SPONDYLOLYSIS

(71) Applicants: Carl P. Giordano, New Vernon, NJ (US); Altus Partners LLC, West Chester, PA (US)

(72) Inventors: Patrick M. White, Rydal, PA (US); Jordan Bucher, Sinking Spring, PA (US); Carl P Giordano, New Vernon, NJ (US); Michael Fitzgerald, Newtown Square, PA (US)

(73) Assignees: Carl P. Giordano, New Vernon, NJ (US); ALTUS PARTNERS LLC, West Chester, PA (US)

( * ) Notice: Subject to any disclaimer, the term of this patent is extended or adjusted under 35 U.S.C. 154(b) by 108 days.

(21) Appl. No.: 16/781,648

(22) Filed: Feb. 4, 2020

(65) Prior Publication Data
US 2020/0253647 A1  Aug. 13, 2020

Related U.S. Application Data

(60) Provisional application No. 62/803,934, filed on Feb. 11, 2019.

(51) Int. Cl.
*A61B 17/70* (2006.01)

(52) U.S. Cl.
CPC ...... *A61B 17/7067* (2013.01); *A61B 17/7071* (2013.01)

(58) Field of Classification Search
CPC ............ A61B 17/7067; A61B 17/7071; A61B 17/7056; A61B 17/7062–17/707
See application file for complete search history.

(56) References Cited

U.S. PATENT DOCUMENTS

| 6,364,883 B1 | 4/2002 | Santilli |
| 9,615,860 B2 | 4/2017 | Giordano |

(Continued)

FOREIGN PATENT DOCUMENTS

| CA | 2823410 C | 9/2018 | |
| EP | 2149341 A2 * | 2/2010 | ......... A61B 17/7032 |

OTHER PUBLICATIONS

English-language translation of EP 2149341 A2; provided by EPO and Google; accessed on Sep. 23, 2021.*

(Continued)

*Primary Examiner* — Julianna N Harvey
(74) *Attorney, Agent, or Firm* — Matthew B. Dernier, Esq.

(57) ABSTRACT

Methods and apparatus provide for: (i) coupling a spinous process plate to one lateral side of a spinous process of a spine of a patient, the spinous process plate extending substantially parallel to a sagittal plane (anterior-posterior plane) through the spine of the patient, the spinous process plate including a first fixation element facilitating a connection of the spinous process plate to the one lateral side of the spinous process; (ii) coupling a laminar plate to a laminar on the one lateral side of the spinous process of the spine, the laminar plate extending transversely from the spinous process plate and transversely to both the sagittal plane and a coronal plane (lateral plane) through the spine of the patient, the laminar plate including a second fixation element facilitating a connection of the laminar plate to the laminar on the one lateral side of the spinous process; (iii) engaging a sub-laminar hook to the laminar on the one lateral side of the spinous process, the sub-laminar hook extending transversely from the laminar plate and substantially parallel to a transverse plane through the spine of the patient, the sub-laminar hook extending and hooking beneath the laminar on the one lateral side of the spinous process of the spine; and (Continued)

(iv) extending a rod toward a pedicle on the one lateral side of the spinous process of the spine of the patient, the rod having proximal and distal ends, the proximal end being connected to the laminar plate and the rod extending from the laminar plate toward the pedicle, where the rod prohibits movement of bone associated with a fracture in a pars interarticularis of a vertebral arch on the one lateral side of the spinous process of the spine.

10 Claims, 7 Drawing Sheets

(56) References Cited

U.S. PATENT DOCUMENTS

| | | | |
|---|---|---|---|
| 9,737,345 B2 | 8/2017 | Giordano | |
| 9,770,270 B2 | 9/2017 | Giordano | |
| 9,913,666 B2 | 3/2018 | Giordano | |
| 2003/0040746 A1 | 2/2003 | Mitchell | |
| 2006/0004363 A1 | 1/2006 | Brockmeyer | |
| 2011/0160772 A1* | 6/2011 | Arcenio | A61F 2/4405 606/248 |
| 2014/0188223 A1* | 7/2014 | Jensen | A61F 2/44 623/17.11 |
| 2015/0196328 A1* | 7/2015 | Hirschl | A61B 17/7056 606/279 |

OTHER PUBLICATIONS

International Search Report and Written Opinion for corresponding PCT Application No. PCT/US2020/016578, 9 pages, dated Apr. 8, 2020.
Altaf, F., et al., "Repair of spondylolysis using compression with a modular link and screws", Journal of bone and joint surgery. British volume, vol. 93, Issue: 1, p. 73-77, Jan. 2011.
Askar, Z., et al., "Scott Wiring for Direct Repair of Lumbar Spondylolysis" Spine—Philadelphia—Harper and Row Publishers Then JB Lippincott Company Then Lippencott Williams and Wilkins, vol. 28, Issue: 4, pp. 354-357, Jan. 1, 2003.
Guy R Fogel, "Repair of pars interarticularis defect with a modified cable-screw construct" Journal Of Surgical Orthopaedic Advances, pp. 1-7, Jun. 2007.
David S Bradford, "Repair of the Defect in Spondylolysis or Minimal Degrees of Spondylolisthesis by Segmental Wire Fixation and Bone Grafting" Spine, vol. 10, No. 7, pp. 673-679, Jan. 1985.
Xiong-sheng Chen, "A Universal Pedicle Screw and V-Rod System for Lumbar Isthmic Spondylolysis: A Retrospective Analysis of 21 Cases" PLoS One 8(5): pp. 1-9, May 17, 2013.
Clegg T., "Clinical Outcomes Following Repair of the Pars Interarticularis" Health Sciences, vol. 42, Issue 2, pp. 72-76, Feb. 2013.
Felix Debusscher, "Direct repair of defects in lumbar spondylolysis with a new pedicle screw hook fixation: clinical, functional and Ct-assessed study" European Spine Journal vol. 16, pp. 1650-1658 May 23, 2007.
Doniel Drazin, M.D., "Direct surgical repair of spondylolysis in athletes: indications, techniques, and outcomes" Neurosurg Focus, vol. 31, pp. 1-12, Nov. 2011.
Gillet, P., Direct Repair of Spondylolysis Without Spondylolisthesis, Using a Rod-Screw Construct and Bone Grafting of the Pars Defect Spine, vol. 24, Issue 12, pp. 1252-1256, Jan. 1999.
Christopher C Gillis, "A minimally invasive approach to defects of the pars interarticularis:Restoring function in competitive athletes" Clinical Neurology and Neurosurgery, vol. 39, pp. 29-34, Aug. 17, 2015.
Akira Hioki, MD, PhD., "Repair of Pars Defects by Segmental Transverse Wiring for Athletes With Symptomatic Spondylolysis" Spine, vol. 37, No. 9, pp. 802-807, Apr. 2012.
Serena S. Hu, MD, et al., "Spondylolisthesis and Spondylolysis" The Journal of Bone & Joint Surgery, vol. 90-A No. 3, pp. 655-671, Mar. 2008.
G,V. Johnson, et al., "The Scott Wiring Technique for Direct Repair of Lumbar Spondylolysis" The Journal of Bone & Joint Surgery, pp. 426-430, Jan. 1992.
Kakiuchi, Masaaki, "Repair of the defect in spondylolysis: Durable fixation with pedicle screws and laminar hooks" Journal of Bone and Joint Surgery; vol. 79, No. 6; pp. 818-825, Jan. 1997.
Karatas, Ali F., "Comparison of Direct Pars Repair Techniques of Spondylolysis in Pediatric and Adolescent Patients: Pars Compression Screw Versus Pedicle Screw-Rod-Hook" Clinical Spine Surgery vol. 29, No. 7, pp. 272-280, Aug. 1, 2016.
Wael M.T. Koptan, MD, "Direct repair of spondylolysis presenting after correction of adolescent idiopathic scoliosis" The Spine Journal, vol. 11, pp. 133-138, Jan. 6, 2011.
Lim, M. R., "Symptomatic spondylolysis: diagnosis and treatment" Current opinion in pediatrics, vol. 16, Issue 1 pp. 37-46, Jan. 2004.
Ian S. Mutchnick, M.D., et al., "Motion segment-sparing repair of symptomatic chronic pars defects" Spine, vol. 15, pp. 159-163, Aug. 2011.
Joseph C. Noggle, et al., "Minimally invasive direct repair of lumbar spondylolysis with a pedicle screw and hook construct" Neurosurg. Focus, vol. 25, pp. 1-6, Aug. 2008.
Ogawa, H., "Clinical Outcome After Segmental Wire Fixation and Bone Grafting for Repair of the Defects in Multiple Level Lumbar Spondylolysis" Journal of spinal disorders & techniques, vol. 20, Issue 1, pp. 521-525, Jan. 1, 2007.
Jonathan H. Oren, M.D., et al., "Pars Injuries in Athletes" Bulletin of the Hospital for Joint Diseases vol. 74, Issue 1, pp. 73-81, Jan. 2016.
Vasudeva S. Paim et al., "Repair of spondylolytic defect with a cable screw reconstruction" International Orthopaedics vol. 32, pp. 121-125, Sep. 8, 2006.
Kristen E. Raddiff, et al., Surgical Management of Spondylolysis and Spondylolisthesis in Athletes: Indications and Return to Play, Current Sports Medicine Reports, vol. 8, No. 1, pp. 35-40, Jan. 2009.
Randall, Rachel M., "Review of Pediatric Spondylolysis and Spondylolisthesis" Sports medicine and arthroscopy reviewm vol. 24, Issue 4, pp. 184-187 Dec. 1, 2016.
Zhao Jian., et al., "Biomechanical and Clinical Study on Screw Hook Fixation After Direct Repair of Lumbar Spondylolysis" Chinese journal of Traumatology vol. 9, Issue 5, pp. 288-292, Jan. 2006.

* cited by examiner

METHODS AND APPARATUS FOR TREATING SPONDYLOLYSIS

CROSS REFERENCE TO RELATED APPLICATIONS

This application claims the benefit of U.S. Provisional Patent Application No.: 62/803,934, filed Feb. 11, 2019, the entire disclosure of which is hereby incorporated by reference.

BACKGROUND OF THE INVENTION

The present invention relates to methods and apparatus for treating spondylolysis.

Spondylolysis is a defect or stress fracture in the pars interarticularis of the vertebral arch. Although the vast majority of cases occur in the lower lumbar vertebrae of the spine (e.g., L5), spondylolysis may also occur in the cervical vertebrae.

Pars stress fractures involve a small connecting bone in the spine, called the pars interarticularis. The pars bone is a small bone that connects the facet joints, the chain of joints found on each side of the spine. The facet joints spread apart and have no pressure on them when the patient is sitting or bending forward; however, they press against each other and are under pressure during activities such as running, jumping, kicking, rotating or arching backward.

Spondylolysis is a common diagnosis that exists in anywhere from about 4-6% of the adolescent (young adult) population. It is believed that both repetitive trauma and an inherent genetic weakness can make an individual more susceptible to spondylolysis. Research supports that there are hereditary and acquired risk factors that can make one more susceptible to spondylolysis. Spondylolysis is generally more prevalent in males compared to females, and tends to occur earlier in males due to their involvement in more strenuous activities at a younger age. In a young athlete, the spine is still growing, which means that there are many ossification centers, leaving points of weakness in the spine. This leaves young athletes at increased risk of spondylolysis, particularly when involved in repetitive hyperextension and rotation across the lumbar spine. Spondylolysis is a common cause of low back pain in preadolescents and adolescent athletes, as it accounts for about 50% of all low back pain.

The rise in athletic participation, as well as the intensity of participation has led to a growing incidence of these stress fractures. Most of these are treated without surgery but 20% of these require surgical intervention. A lot of these are treated by benign neglect primarily because no great techniques exist to repair this stress fracture. The L4 spondylolysis untreated increases the stress on the L4-5 disc space to 120% and the untreated L5 spondylolysis untreated increases the stress on the L5-S1 disc space to 168%. Repair of the lysis returns the stress on the disc caused by the spondylolysis to near normal, thereby preventing disc degeneration and back pain.

Significant numbers, perhaps even all of the adult isthmic spondylolisthesis that are fused with pedicle screws and interbody fusions are essentially adult manifestations of an untreated adolescent spondylolysis. Unfortunately, many of these become symptomatic in adulthood when people have already determined their livelihood. Many times after the lumbar fusion for spondylolisthesis, patients do recover and are markedly improved but may be left with restrictions that prevent them from returning to their profession. Frequently this leads to permanent restrictions and ultimately burdens society and the disability system.

Current techniques to repair a pars interarticularis stress fracture include wires and cables, repair with pedicle screw and a curved rod under the spinous process, pedicle screws, or a rod hook construct under the lamina.

Although the conventional techniques may yield some degree of improvement, they are crude and have limitations. None of the conventional techniques that presently exist provide sufficient segmental rigid multi-planar fixation. The conventional techniques also have secondary side effects, as they encroach and disrupt neighboring facet joints. Alteration of the anatomy resulting from the conventional techniques may lead to foramina stenosis and postoperative radiculopathy. The conventional techniques also require sizable implants that may become painful hardware in the young thin gymnast or a thin patient.

The problems associated with the conventional techniques for repair a pars interarticularis stress fracture have led surgeons to shy away from treating spondylolysis surgically. The lack of a superior surgical technique has also led to practitioners recommending that patients live with residual symptoms and refrain from sports or other risky activities. The current recommendation for patients with this diagnosis include: 1) Elimination of all activities and wear a lumbo-sacral orthosis for three months (if the fracture heals, then the patients may resume all activities). 2) If the fracture does not heal, avoid certain sports and activities, and consider occupations that avoid manual labor. For patients that have mild residual symptoms, accept the residuals, and find coping mechanisms. 3) Patients that fail to heal and remain symptomatic are typically treated surgically.

Accordingly, there are needs in the art for improved methods and apparatus for treating spondylolysis.

SUMMARY OF THE INVENTION

In accordance with one or more embodiments of the invention, methods and apparatus provide for coupling a spinous process plate to one lateral side of a spinous process of a spine of a patient, the spinous process plate extending substantially parallel to a sagittal plane (anterior-posterior plane) through the spine of the patient, the spinous process plate including a first fixation element facilitating a connection of the spinous process plate to the one lateral side of the spinous process.

The methods and apparatus may further provide for coupling a laminar plate to a laminar on the one lateral side of the spinous process of the spine, the laminar plate extending transversely from the spinous process plate and transversely to both the sagittal plane and a coronal plane (lateral plane) through the spine of the patient, the laminar plate including a second fixation element facilitating a connection of the laminar plate to the laminar on the one lateral side of the spinous process.

The methods and apparatus may still further provide for engaging a sub-laminar hook to the laminar on the one lateral side of the spinous process, the sub-laminar hook extending transversely from the laminar plate and substantially parallel to a transverse plane through the spine of the patient, the sub-laminar hook extending and hooking beneath the laminar on the one lateral side of the spinous process of the spine.

The methods and apparatus may still further provide for extending a rod toward a pedicle on the one lateral side of the spinous process of the spine of the patient, the rod having proximal and distal ends, the proximal end being connected to the laminar plate and the rod extending from the laminar plate toward the pedicle.

Preferably, the rod prohibits movement of bone associated with a fracture in a pars interarticularis of a vertebral arch on the one lateral side of the spinous process of the spine.

The methods and apparatus may still further provide that the first fixation element includes a first aperture through the spinous process plate and a first anchoring element extending through the first aperture and into the one lateral side of the spinous process, thereby facilitating the connection of the spinous process plate to the spinous process of the spine.

The methods and apparatus may still further provide that the second fixation element includes a second aperture through the laminar plate and a second anchoring element extending through the second aperture and into the laminar on the one lateral side of the spinous process, thereby facilitating the connection of the laminar plate to the laminar of the spine.

The methods and apparatus may still further provide for coupling the distal end of the rod to the pedicle on the one lateral side of the spinous process of the spine of the patient via a third fixation element.

The methods and apparatus may still further provide that the third fixation element includes a tulip coupled to the pedicle via a pedicle screw, and a locking element fixing the distal end of the rod to the tulip.

The methods and apparatus may still further provide that the spinous process plate extends in a first plane, the laminar plate extends in a second plane, and the first and second planes are at an obtuse angle with respect to one another.

The methods and apparatus may still further provide that the obtuse angle is one of: (i) between 90 degrees and about 140 degrees; (ii) between 90 degrees and about 130 degrees; (iii) between 90 degrees and about 120 degrees; (iv) between about 100 degrees and about 120 degrees; and (v) about 110 degrees.

The methods and apparatus may still further provide that the laminar plate includes an axis extending substantially parallel to the transverse plane of the patient, and the rod includes a longitudinal axis extending from the laminar plate at an obtuse angle with respect to the axis.

The methods and apparatus may still further provide that the obtuse angle is one of: (i) between about 120 degrees and about 160 degrees; (ii) between about 130 degrees and about 150 degrees; and (iii) about 140 degrees.

The methods and apparatus may still further provide that the spinous process plate, the laminar plate, and the rod are sized and shaped to connect to a lumbar vertebrae of the spine of the patient.

Other aspects, features, and advantages of the present invention will be apparent to one skilled in the art from the description herein taken in conjunction with the accompanying drawings.

DESCRIPTION OF THE DRAWINGS

For the purposes of illustration, there are forms shown in the drawings that are presently preferred, it being understood, however, that the invention is not limited to the precise arrangements and instrumentalities shown.

DETAILED DESCRIPTION OF THE PREFERRED EMBODIMENTS

Figure 1:
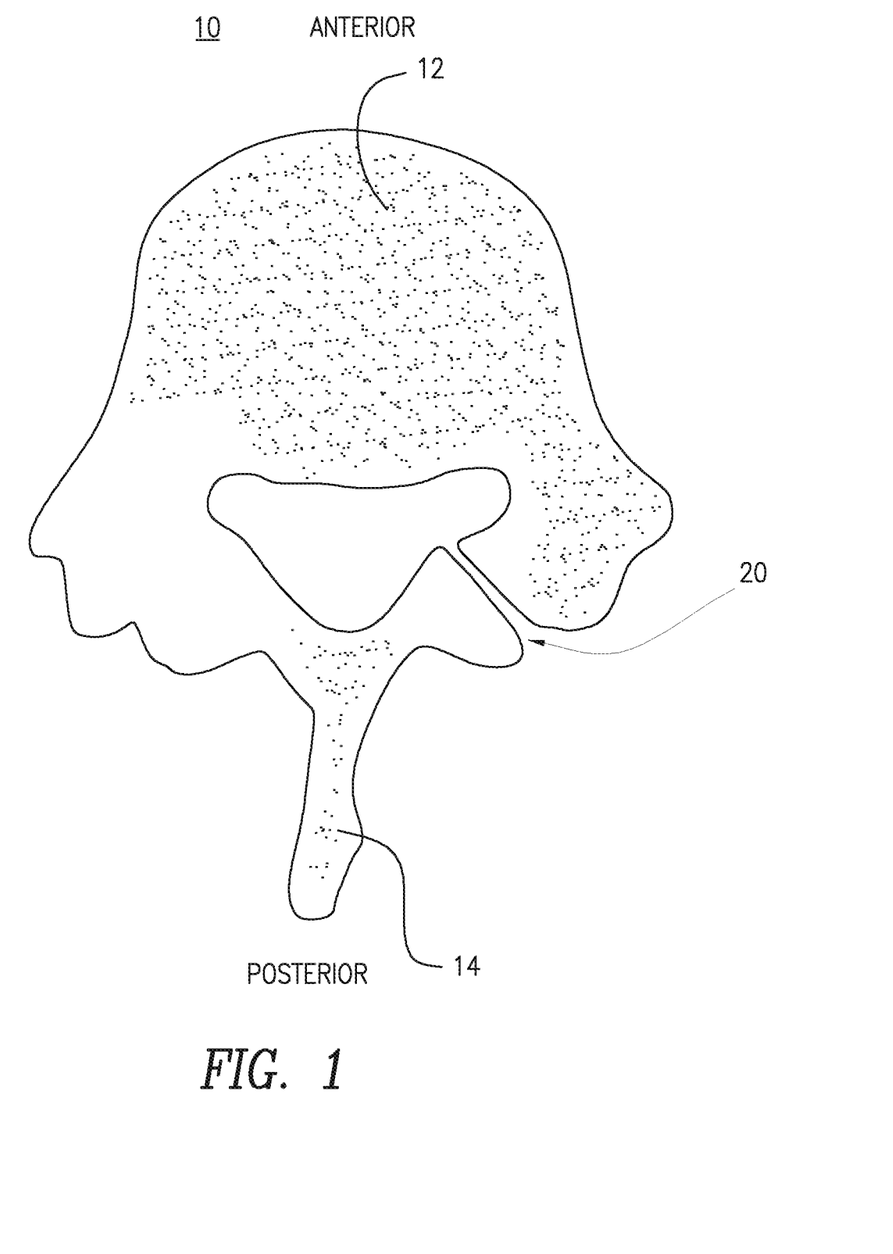
FIG. 1 is a view of a patient's vertebrae in the transverse plane, where the patient suffers from a pars fracture.

With reference to the drawings wherein like numerals indicate like elements there is shown in FIG. 1 a view of a patient's vertebrae 12 in the transverse (axial) plane, where the patient suffers from a pars fracture 20. As is the general case, the fracture 20 is located in the pars interarticularis, which connects the facet joints at respective lateral sides of the spinous process 14.

Figure 2:
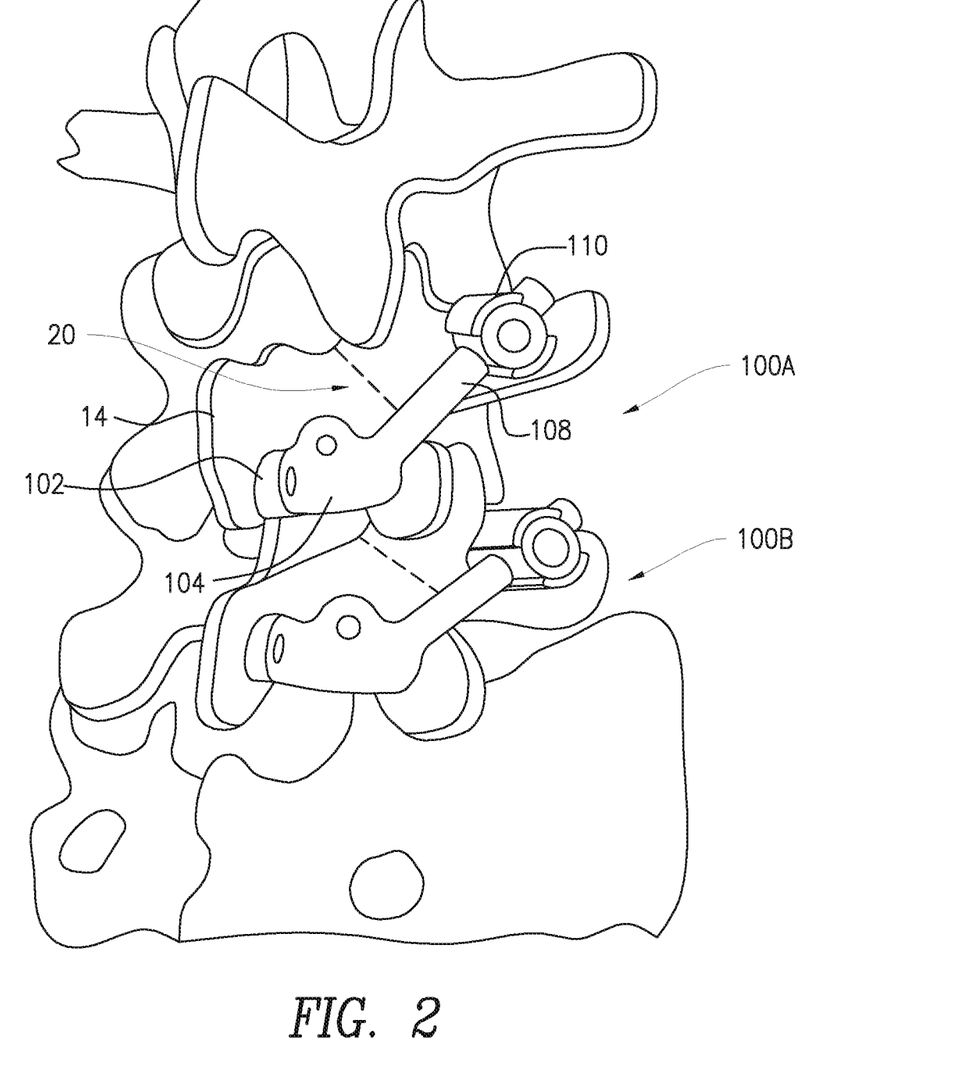
FIG. 2 is a posterior view of a model of a lumbar spine on which first and second pars plate apparatus have been attached to respective levels, in order to simulate surgical treatment of respective pars fractures at each level.
Figure 3:
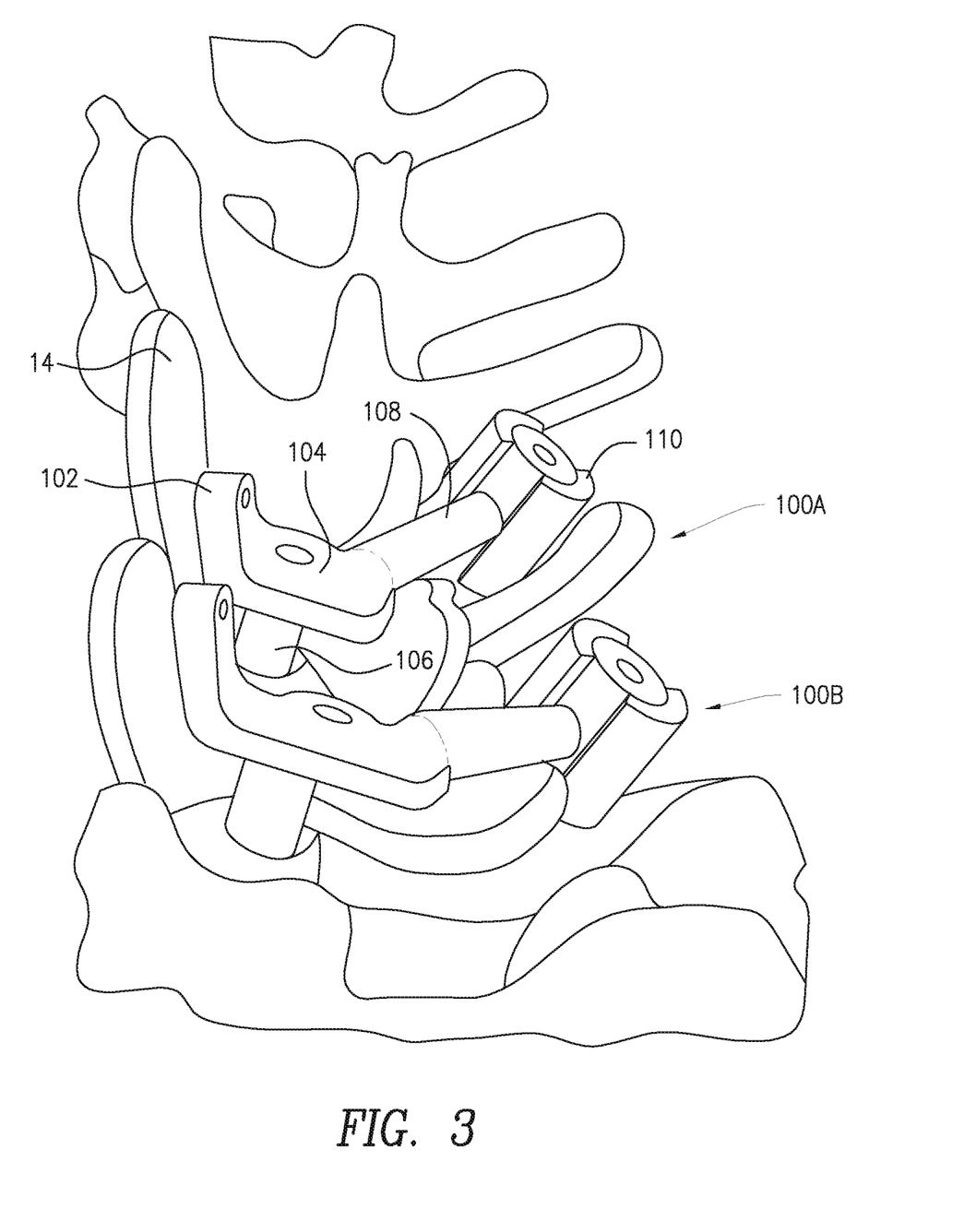
FIG. 3 is an alternative posterior view of the arrangement of FIG. 2.

FIG. 2 is a posterior view of a model of a lumbar spine of a patient on which a first pars plate apparatus 100A and a second pars plate apparatus 100B have been attached at respective levels. Each of the first and second pars plate apparatus 100A, 100B traverse a respective fracture 20. FIG. 3 is an alternative posterior view of the arrangement of FIG. 2.

Figure 4:
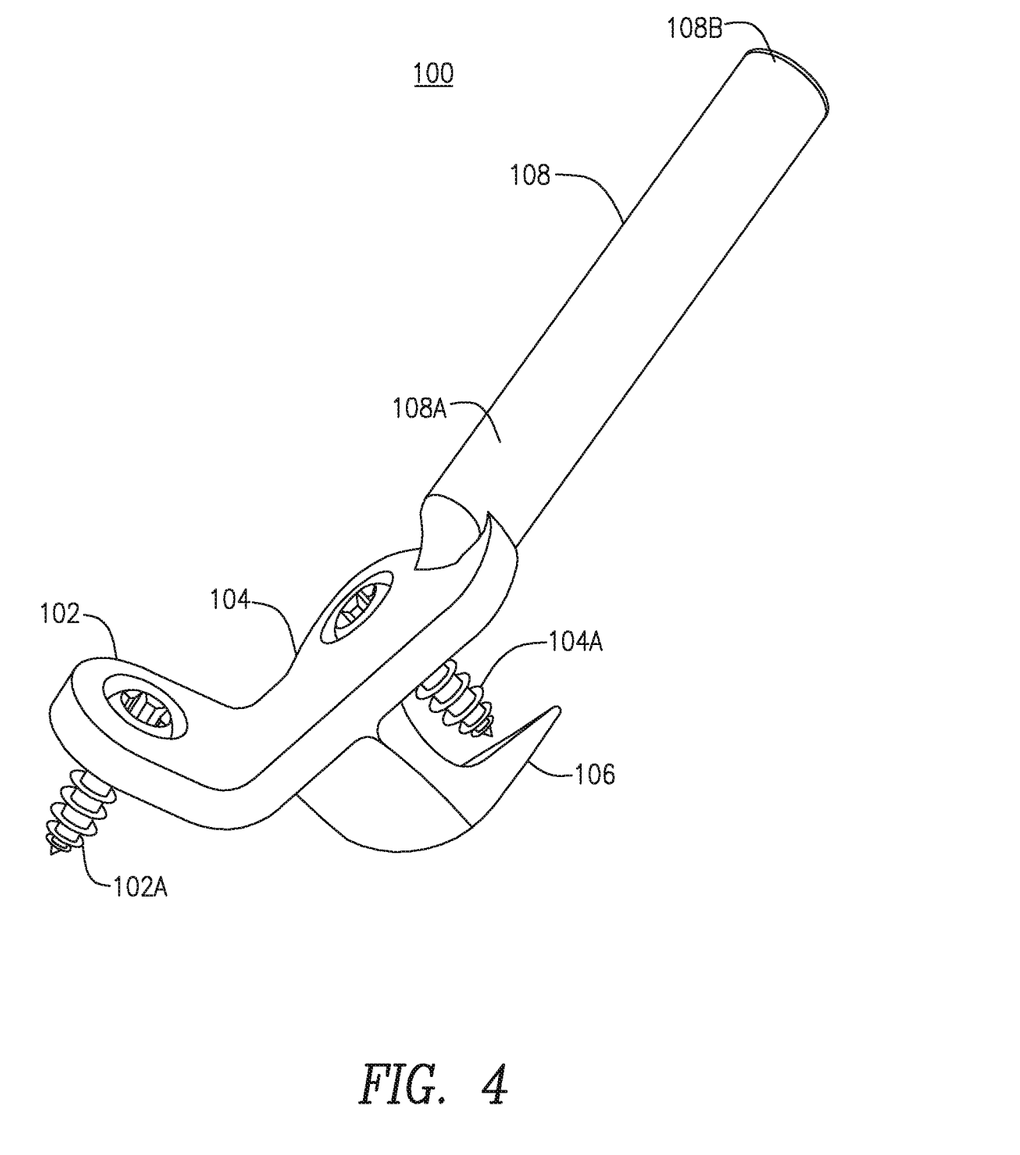
FIG. 4 is a perspective view of a pars plate apparatus in accordance with one or more embodiments of the invention.
Figure 5:
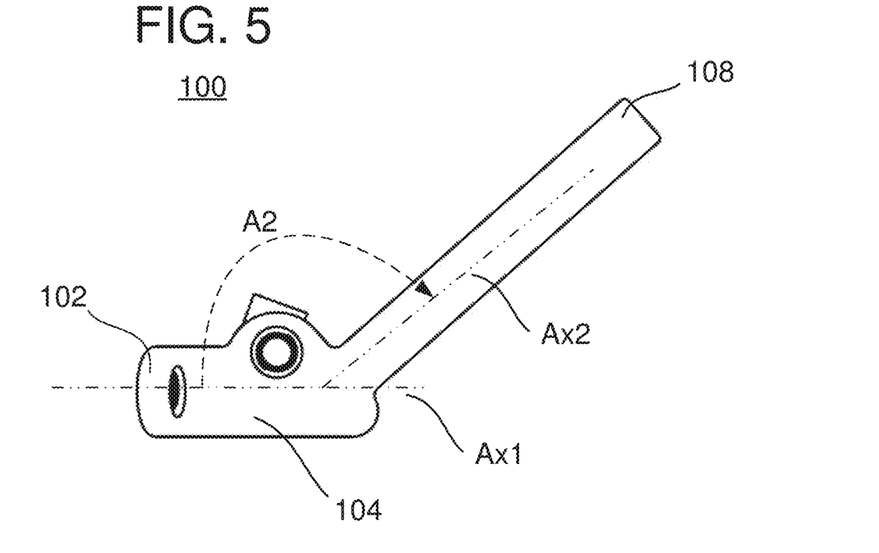
FIG. 5 is a posterior view of the pars plate apparatus in accordance with one or more embodiments of the invention.
Figure 6:
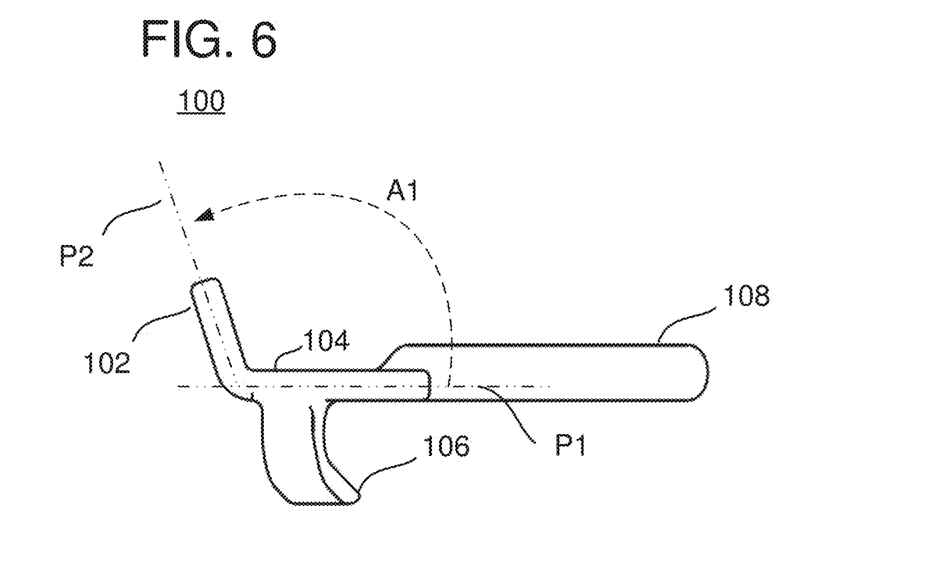
FIG. 6 is a transverse view of the pars plate apparatus in accordance with one or more embodiments of the invention.

Some details regarding the design and function of the respective first and second pars plate apparatus 100A, 100B will now be presented with reference to FIGS. 4, 5, and 6. FIG. 4 is a perspective view of an apparatus 100 in accordance with one or more embodiments of the invention. FIG. 5 is a posterior view of the pars plate apparatus 100, and FIG. 6 is a transverse view of the pars plate apparatus 100.

The pars plate apparatus 100 includes a spinous process plate 102, a laminar plate 104, a sub-laminar hook 106, and a rod 108. The spinous process plate 102, the laminar plate 104, and the rod 108 are sized, shaped, and interoperable to connect to a vertebrae of the spine of the patient, such as the lumbar spine.

The spinous process plate 102 extends substantially parallel to the sagittal plane (anterior-posterior plane) through a spine of the patient when implanted. The spinous process plate 102 includes at least one first fixation element 102A facilitating a connection of the spinous process plate 102 to one lateral side of the spinous process 14 of the spine. For example, the first fixation element 102A may include a first aperture through the spinous process plate 102 and a first anchoring element (such as a nail, screw, or the like) extending through the first aperture and into the one lateral side of the spinous process 14, thereby facilitating the connection of the spinous process plate 102 to the spinous process 14 of the spine.

The laminar plate 104 extends transversely from the spinous process plate 102 and transversely to both the sagittal plane and the coronal plane (lateral plane) through the spine of the patient when implanted. The laminar plate 104 includes at least one second fixation element 104A facilitating a connection of the laminar plate 104 to a laminar on the one lateral side of the spinous process 14 of the spine. For example, the second fixation element 104A may include a second aperture through the laminar plate 104 and a second anchoring element (such as a nail, screw, or the like), extending through the second aperture and into the laminar 16 on the one lateral side of the spinous process 14, thereby facilitating the connection of the laminar plate 104 to the laminar 16 of the spine.

The sub-laminar hook 106 extends transversely from the laminar plate 104 and substantially parallel to the transverse (axial) plane through the spine of the patient when implanted. The sub-laminar hook 106 is sized and shaped to extend and hook beneath the laminar 16 on the one lateral side of the spinous process 14 of the spine.

The rod 108 includes a proximal end 108A and a distal end 108B, the proximal end 108A being connected to the laminar plate 104 and the rod extending from the laminar plate 104 toward a pedicle on the one lateral side of the spinous process 14 of the spine when implanted. The rod 108 is sized shaped and anchored (as discussed later) to prohibit movement of bone associated with the fracture 20 in the pars interarticularis of the vertebral arch.

Figures 7, 8, 9:
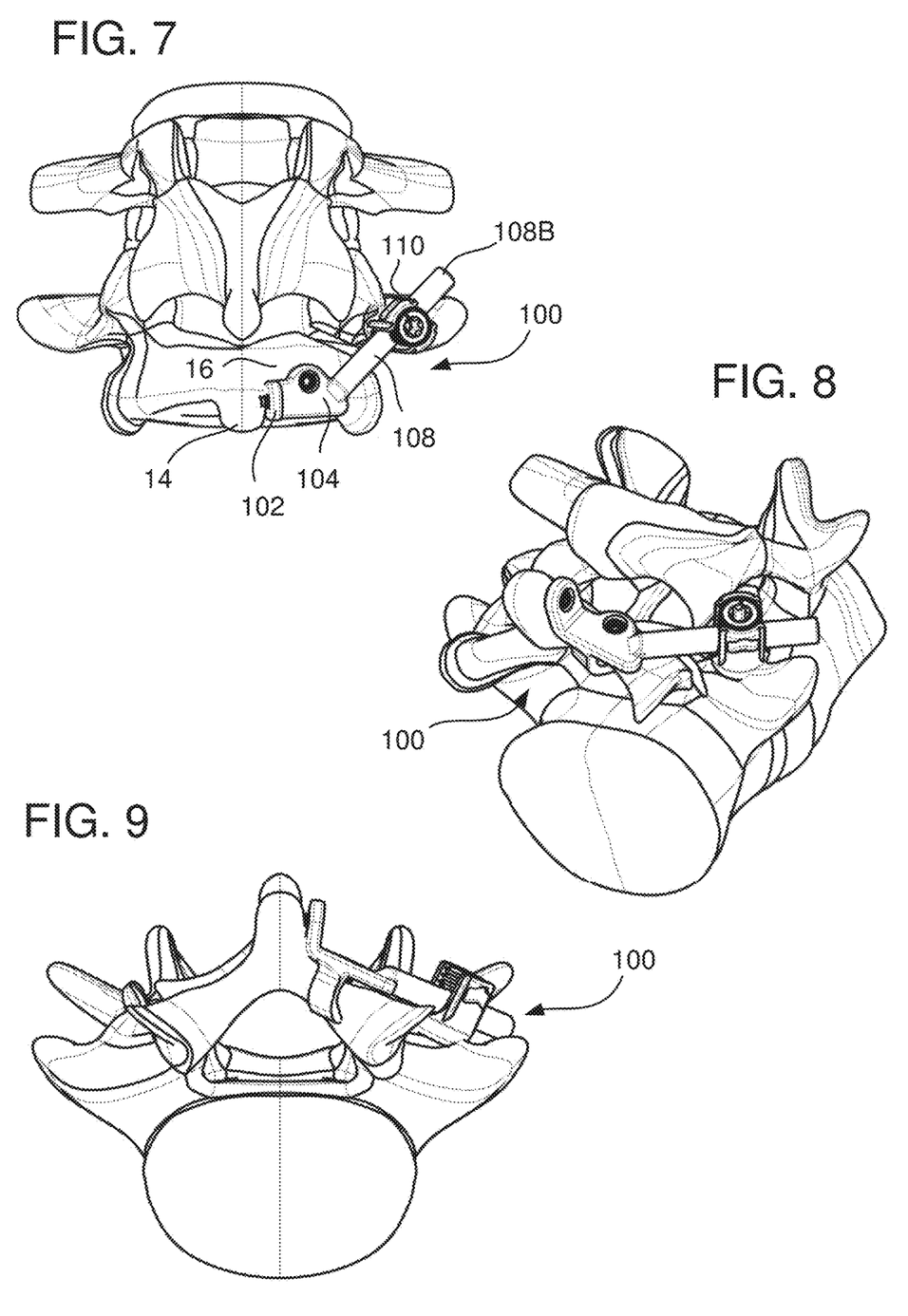
FIG. 7 is a posterior view of a lumbar spine on which a pars plate apparatus is disposed on a patient's spine in order to treat a pars fracture.
FIG. 8 is an alternative posterior-transverse perspective view of the arrangement of FIG. 7.
FIG. 9 is an transverse view of the arrangement of FIG. 7.
Figure 10:
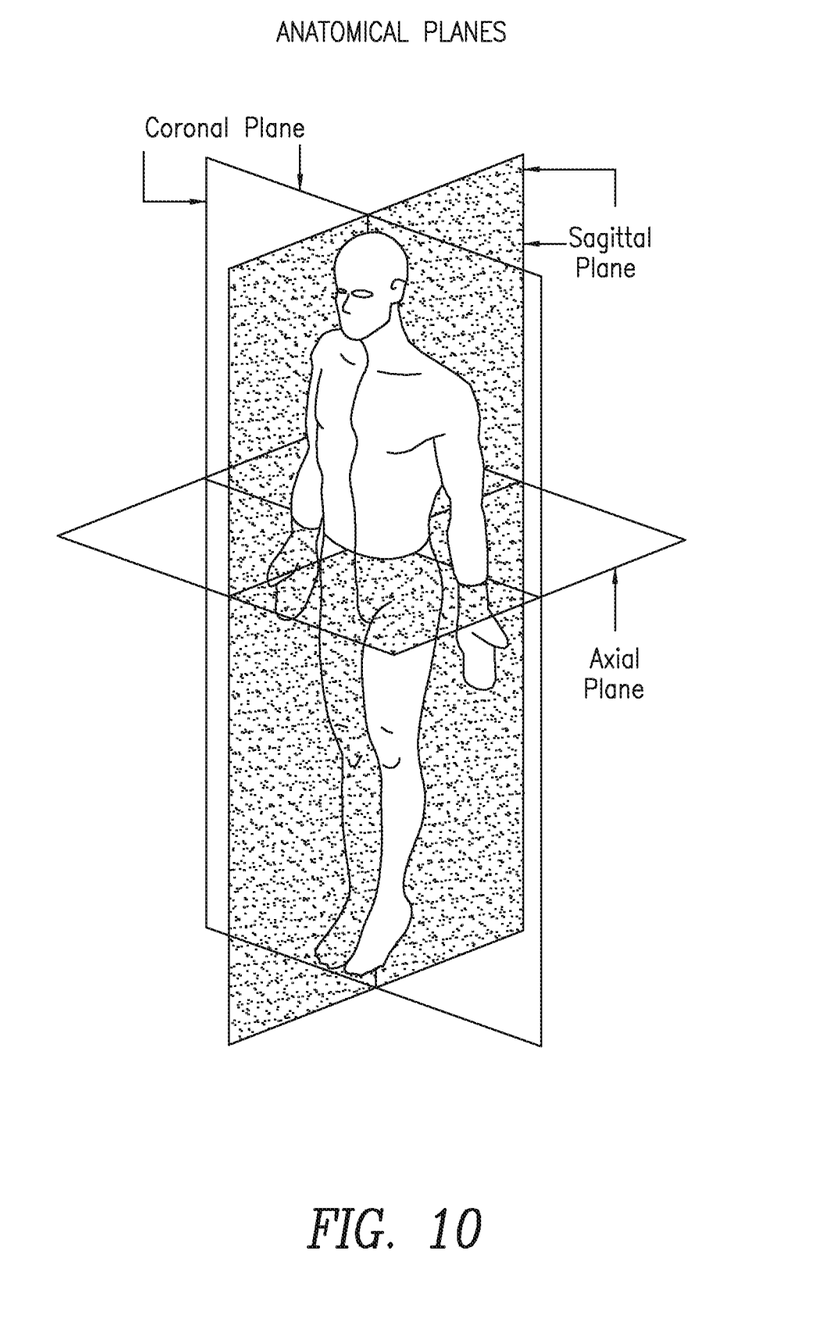
FIG. 10 is an anatomical schematic diagram showing the respective coronal plane, sagittal plane, and axial (or transverse) plane of the human anatomy as used herein.

Reference is now made to FIGS. 7, 8 and 9, where FIG. 7 is a posterior view of the lumbar spine on which the pars plate apparatus 100 is disposed, FIG. 8 is an alternative posterior-transverse perspective view of the arrangement of FIG. 7, and FIG. 9 is an transverse view of the arrangement of FIGS. 7 and 8. As best seen in FIG. 7, the pars plate apparatus 100 includes at least one third fixation element 110 coupling the distal end 108B of the rod 108 to the pedicle on the one lateral side of the spinous process 14 of the spine when implanted. For example, the third fixation element 110 may include a tulip coupled to the pedicle via a pedicle screw, and a locking element fixing the distal end 108B of the rod 108 to the tulip.

As best seen in FIGS. 5 and 6, the spinous process plate 102 extends in a first plane P1, the laminar plate 104 extends in a second plane P2, and the first and second planes P1, P2 are at an obtuse angle A1 with respect to one another. For example, the obtuse angle A may be one of: (i) between 90 degrees and about 140 degrees; (ii) between 90 degrees and about 130 degrees; (iii) between 90 degrees and about 120 degrees; (iv) between about 100 degrees and about 120 degrees; and (v) about 110 degrees.

Also as best seen in FIGS. 5 and 6, the laminar plate 104 includes an axis Ax1 extending substantially parallel to the transverse plane of the patient, and the rod 108 includes a longitudinal axis Ax2 extending from the laminar plate 104 at an obtuse angle A2 with respect to the axis Ax1. For example, the obtuse angle A2 may be one of: (i) between about 120 degrees and about 160 degrees; (ii) between about 130 degrees and about 150 degrees; and (iii) about 140 degrees.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for treating a fracture in a pars interarticularis of a vertebral arch on a lateral side of a spinous process of a spine of a patient, the fracture having a length and defining a first part of the fractured pars interarticularis and a second part of the fractured pars interarticularis, the apparatus, comprising:
    a spinous process plate extending substantially parallel to a sagittal plane through the spine when implanted, the spinous process plate including a first fixation element configured to pass through the spinous process plate and into the lateral side to attach the spinous process plate to the lateral side when implanted;
    a laminar plate extending transversely from the spinous process plate and transversely to both the sagittal plane and a coronal plane through the spine when implanted, the laminar plate including a second fixation element configured to pass through the laminar plate and into a laminar to attach the laminar plate to the laminar on the lateral side when implanted;
    a sub-laminar hook extending transversely from the laminar plate and substantially parallel to a transverse plane through the spine when implanted, the sub-laminar hook configured to extend and hook beneath the laminar on the lateral side and abut the first part of the fractured pars interarticularis; and
    a rod having proximal and distal ends, the proximal end being connected to the laminar plate and the rod extending substantially perpendicular to the length of the fracture from the laminar plate toward a pedicle on the lateral side when implanted,
    wherein the rod is anchored at the distal end to a third fixation element extending substantially perpendicular to a longitudinal axis of the rod in a configuration that couples the distal end of the rod to the second part of the fractured pars interarticularis and causes the sub-laminar hook and the rod to prohibit movement of the first and second parts of the fractured pars interarticularis relative to one another when implanted.

2. The apparatus of claim 1, wherein the spinous process plate includes a first aperture and the first fixation element includes a first anchoring element extending through the first aperture and configured to extend into the lateral side, thereby facilitating the attachment of the spinous process plate to the spinous process when implanted.

3. The apparatus of claim 1, wherein the laminar plate includes a second aperture and the second fixation element includes a second anchoring element extending through the second aperture and configured to extend into the laminar on the lateral side, thereby facilitating the attachment of the laminar plate to the laminar when implanted.

4. The apparatus of claim 1, wherein the third fixation element couples the distal end of the rod to the pedicle on the lateral side when implanted.

5. The apparatus of claim 4, wherein the third fixation element includes a tulip configured to couple to the pedicle via a pedicle screw when implanted, and a locking element fixing the distal end of the rod to the tulip.

6. The apparatus of claim 1, wherein the spinous process plate extends in a first plane, the laminar plate extends in a second plane, and the first and second planes are at an obtuse angle with respect to one another.

7. The apparatus of claim 6, wherein the obtuse angle is one of: (i) between 90 degrees and about 140 degrees; (ii) between 90 degrees and about 130 degrees; (iii) between 90 degrees and about 120 degrees; (iv) between about 100 degrees and about 120 degrees; and (v) about 110 degrees.

8. The apparatus of claim 1, wherein the laminar plate includes an axis configured to extend substantially parallel to the transverse plane of the patient when implanted, and the rod includes a longitudinal axis extending from the laminar plate at an obtuse angle with respect to the axis.

9. The apparatus of claim 8, wherein the obtuse angle is one of: (i) between about 120 degrees and about 160 degrees; (ii) between about 130 degrees and about 150 degrees; and (iii) about 140 degrees.

10. The apparatus of claim 1, wherein the spinous process plate, the laminar plate, and the rod are sized and shaped to connect to a lumbar vertebrae of the spine.

\* \* \* \* \*